US00PP07938P

United States Patent [19]

Hanes

[11] Patent Number: Plant 7,938

[45] Date of Patent: Aug. 11, 1992

[54] GERANIUM NAMED AMERICANA LIGHT PINK

[75] Inventor: Mitchell Hanes, Morgan Hill, Calif.

[73] Assignee: Goldsmith Seeds, Inc., Gilroy, Calif.

[21] Appl. No.: 656,710

[22] Filed: Feb. 19, 1991

[51] Int. Cl.[5] ..... A01H 5/00

[52] U.S. Cl. ..... Plt./87.12

[58] Field of Search ..... Plt./68

*Primary Examiner*—James R. Feyrer

[57] ABSTRACT

A new Geranium cultivar particularly distinguished by the semi-double flowers which are bi-colored; each flower being light pink with a darker colored pink spot near the base of each petal. The plant itself is a strong upright dense bush having a vigorous and fast-rooting growth habit and growing to a height of 11 to 12 cm. as a 5½ inch potted plant. The bi-colored flowers are long lasting, the color changing little with age.

1 Drawing Sheet

BACKGROUND OF THE NEW PLANT

The present invention comprises a new and distinct cultivar of Geranium, botanically known as *Pelargonium hortorum* Bailey. The new cultivar is propagated from a seedling resulting from the cross of a white flower seed parent "Bianca" and a pink colored pollen parent "Blues" (U.S. Plant Pat. No. 5,373).

This new plant is a product of a planned breeding program intended to create new Geranium cultivars with: bi-colored flowers that are light pink with a darker colored pink spot near the base of the petals, semi-double flower form, green foliage, vigorous growth and superior cutting productivity.

The new cultivar was created in 1988 in Gilroy, Calif. and has been repeatedly asexually reproduced by cuttings in Gilroy, Calif. and Guatemala over a two year period. It has also been trialed at Okemos, Mich. It has been found to retain its distinctive characteristics through successive propagations; and this novelty appears to be firmly fixed.

DESCRIPTION OF THE DRAWING

This new Geranium plant is illustrated by the accompanying photographic drawing which shows blooms, buds, and foliage of the plant in full color, the colors shown being as true as can be reasonably obtained by conventional photographic procedures.

DESCRIPTION OF THE NEW CULTIVAR

The following detailed description set forth the distinctive characteristics of this new geranium. The data which defines these characteristics were collected from asexual reproductions carried out in Gilroy, Calif. The plant history was taken on 20 week old plants, blossomed under natural light in a greenhouse. Color readings were taken in the greenhouse on May 29, 1990 at 2 P.M. under ambient light. Color references are primarily to the R.H.S. Colour Chart of The Royal Horticultural Society of London (R.H.S.).

THE PLANT

Classification:

*Botanical.*—*Pelargonium hortorum* Bailey.

*Commercial.*—Zonal geranium.

Form: Strong upright dense bush.

Height: Eleven to twelve cm. as a 5½ inch potted plant, excluding blooms.

Growth: Vigorous and fast-rooting.

Strength: Good shipping ability as rooted or uprooted cuttings.

Foliage: Abundant quantity.

Leaves:

*Size.*—Diameter about 6 to 8 cm.

*Shape.*—Rounded cordate with occasional upfolding between veins.

*Margin.*—Irregularly crenate.

*Texture.*—Leathery and pubescent on both surfaces, especially along veins.

*Ribs and veins.*—Distinctly palmate, 4 to 6 cm. long.

*Color.*—Upper side: Green Under side: Lighter green color. Ribs and veins not prominently different from upper surface.

Petioles: About 2.5 to 7.0 cm. in length with most at about 4.5 cm.

THE BUD

Size:

*Diameter.*—About 8 mm.

*Length.*—About 1.7 cm. to 1.9 cm. at time of bud opening.

Shape: Pointed ovoid.

Color: Of petals when sepals first divide, R.H.S. 49-D.

Sepals: Five in number, flat behind petals, pointed linear lanceolate, R.H.S. 144-B in an open flower.

THE FLOWER

Blooming habit: Continuous throughout the year.

Size: Approximately 4.5 cm. diameter, 1.5 cm. deep, irregularly radially symmetrical.

Form: Cup-shaped when bloom first opens, later flattening to a shallow cup with maturity.

Petals: Six imbricate outer petals, 2.0–2.5 cm. wide and approximately 2.6 cm. long, 3 to 4 inner smaller petaloids of varying shape. Both the outer petals and inner petaloids are light pink, R.H.S. 73-D, with all of the outer petals having the darker colored spot pigment, R.H.S. 57-D, and with some of the inner petaloids have this spot. Veins slightly darker than interveinal regions. Color changing little with age. Underside of petals lighter. Petals and petaloids soft and satiny.

Pedicel: Approximately 2.5 cm. in length.

Persistence: Nonshattering flower.

INFLORESCENCE

Type: An umbel composed of approximately 25 to 30 flowers, erect or laterally ascending.

Peduncle: Approximately 8–12 cm. in length, mostly 9 cm. green in color and sometimes having a light red tint on the surface facing the sun.

REPRODUCTIVE ORGANS

Stamens:

*Anthers.*—Seven to ten positioned below the mature stigma, dull red prior to anthesis.

*Filaments.*—White with a faint blush near the anther.

*Pollen.*—Orange in color.

Pistil:

*Number.*—One.

*Length.*—Approximately 8 mm.

Stigma: Five or six linear lobes of near equal length, curling back toward ovary, pink.

Style:

*Length.*—About 3.0–3.5 mm., color: reddish at the basal end and pink at the distal end.

Ovaries: At anthesis, densely pubescent with white hairs, oblong. Green drying to a light brown at maturity.

Fruit: Partially fertile.

I claim:

1. A new and distinct Geranium cultivar substantially as herein shown and described characterized by green foliage with bi-colored light pink flowers with a distinct deeper colored spot near the center of the outer petals, the flowers being semi-double and borne on the large umbels of the plant that is fast rooting with a dense bush like growth habit.

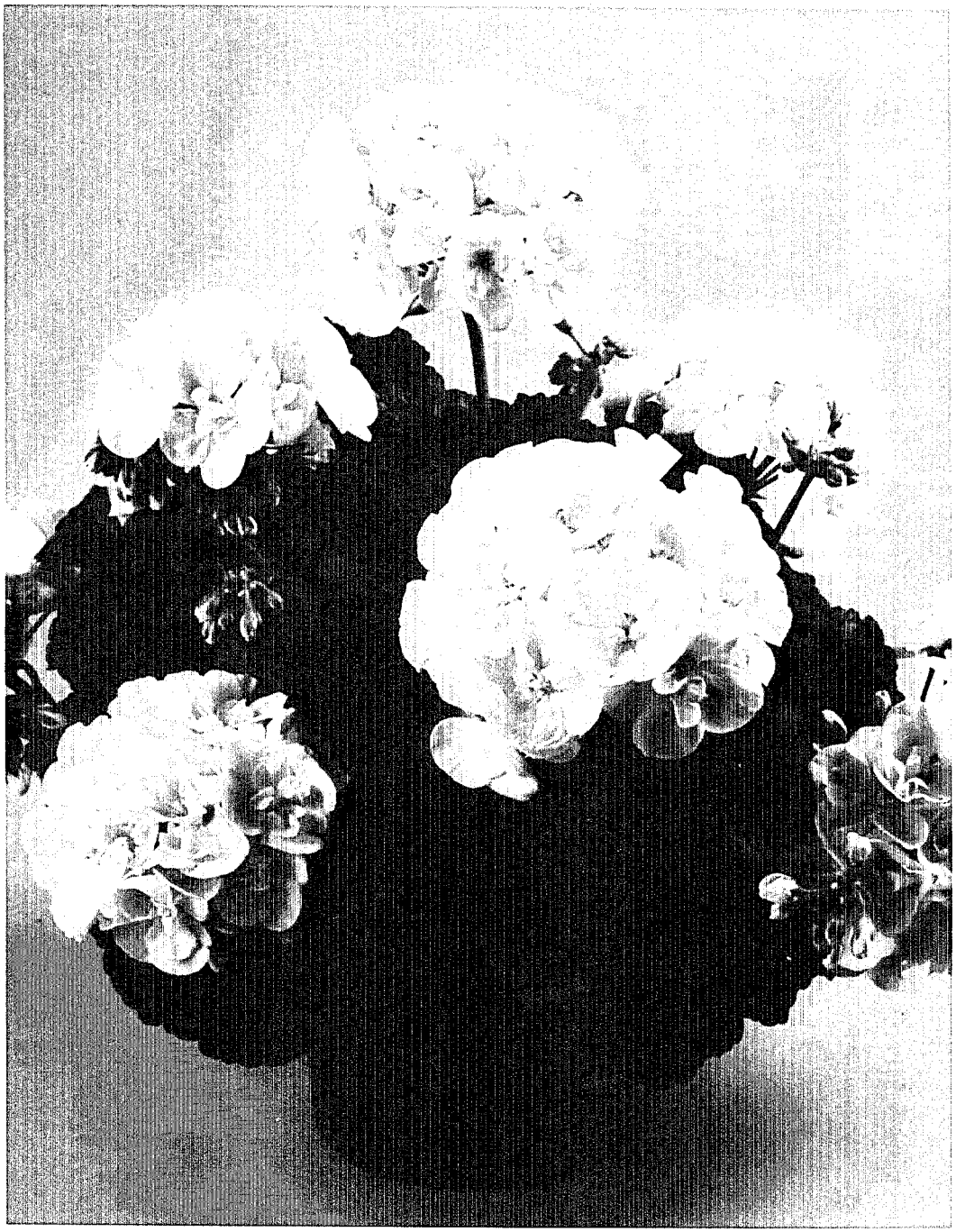

* * * * *